US012778929B2

(12) United States Patent
Dube et al.

(10) Patent No.: US 12,778,929 B2
(45) **Date of Patent: *Nov. 3, 2026**

(54) STABLE PHARMACEUTICAL COMPOSITIONS OF EDARAVONE

(71) Applicant: Slayback Pharma LLC, Princeton, NJ (US)

(72) Inventors: Sushant Omprakash Dube, Navi Mumbai (IN); Girish G. Kore, Solapur (IN); Abhijit Balaji Pawar, Hadolti (IN); Jagdish Lotan Lohar, Pimpri-Chinchwad (IN); Praveen Kumar Subbappa, Princeton, NJ (US); Sumitra Ashokkumar Pillai, Hyderabad (IN); Parvateesam Yenda, Srikakulam (IN); Satheesh Balasubramanian, Hyderabad (IN)

(73) Assignee: Azurity Pharmaceuticals, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/387,735

(22) Filed: Nov. 13, 2025

(65) Prior Publication Data

US 2026/0069570 A1 Mar. 12, 2026

Related U.S. Application Data

(63) Continuation of application No. 19/207,816, filed on May 14, 2025, now Pat. No. 12,491,178, which is a (Continued)

(30) Foreign Application Priority Data

Feb. 16, 2023 (IN) ............................ 202341010407

(51) Int. Cl.
*A61K 31/4152* (2006.01)
*A61K 9/00* (2006.01)
(Continued)

(52) U.S. Cl.
CPC ........ *A61K 31/4152* (2013.01); *A61K 9/0053* (2013.01); *A61K 9/08* (2013.01);
(Continued)

(58) Field of Classification Search
CPC ..... A61K 31/4152; A61K 9/0053; A61K 9/08
See application file for complete search history.

(56) References Cited

U.S. PATENT DOCUMENTS 11,020,375 B2 † 6/2021 Zhou
11,241,416 B2 † 2/2022 Hayama
(Continued)

FOREIGN PATENT DOCUMENTS

JP 4850426 B2 9/2006
JP 4850426 † 10/2011

OTHER PUBLICATIONS

International Preliminary Examination Report, Aug. 15, 2025.
(Continued)

*Primary Examiner* — San Ming R Hui
(74) *Attorney, Agent, or Firm* — Parker Poe Adams & Bernstein, LLP; Paul E. Dietze

(57) ABSTRACT

The present invention relates to liquid pharmaceutical compositions of edaravone. More specifically, stable solutions of edaravone for enteral administration are provided, wherein the composition is stable for extended period of time. The present invention further relates to stable solutions of edaravone, methods for their administration, processes for their production, and use of these compositions for treatment of diseases treatable by edaravone.

18 Claims, 3 Drawing Sheets

Related U.S. Application Data continuation of application No. 19/174,002, filed on Apr. 9, 2025, which is a continuation of application No. 18/340,067, filed on Jun. 23, 2023, now Pat. No. 12,343,330.

(51) Int. Cl.

| | |
|---|---|
| ***A61K 9/08*** | (2006.01) |
| ***A61K 47/02*** | (2006.01) |
| ***A61K 47/10*** | (2017.01) |
| ***A61K 47/12*** | (2006.01) |
| ***A61K 47/20*** | (2006.01) |
| ***A61K 47/26*** | (2006.01) |
| ***A61K 47/34*** | (2017.01) |
| ***A61K 47/36*** | (2006.01) |
| ***A61K 47/38*** | (2006.01) |

(52) U.S. Cl.

CPC .............. *A61K 47/02* (2013.01); *A61K 47/10* (2013.01); *A61K 47/12* (2013.01); *A61K 47/20* (2013.01); *A61K 47/26* (2013.01); *A61K 47/34* (2013.01); *A61K 47/36* (2013.01); *A61K 47/38* (2013.01)

(56) References Cited

U.S. PATENT DOCUMENTS

| | | | |
|---|---|---|---|
| 2022/0105000 | A1 | 4/2022 | Mandal et al. |
| 2022/0409588 | A1 | 12/2022 | Mahendrabhai et al. |

OTHER PUBLICATIONS

Parikh A, Kathawala K, Tan CC, Garg S, Zhou XF. Lipid-based nanosystem of edaravone: development, optimization, characterization and in vitro/in vivo evaluation. Drug Deliv. Nov. 2017;24(1):962-978. doi 10.1080/10717544.2017.1337825.†

Price, D. J., et al. (2018). Approaches to increase mechanistic understanding and aid in the selection of precipitation inhibitors for supersaturating formulations—a PEARRL review. Journal of Pharmacy and Pharmacology, 71(4), 483-509.†

† cited by third party

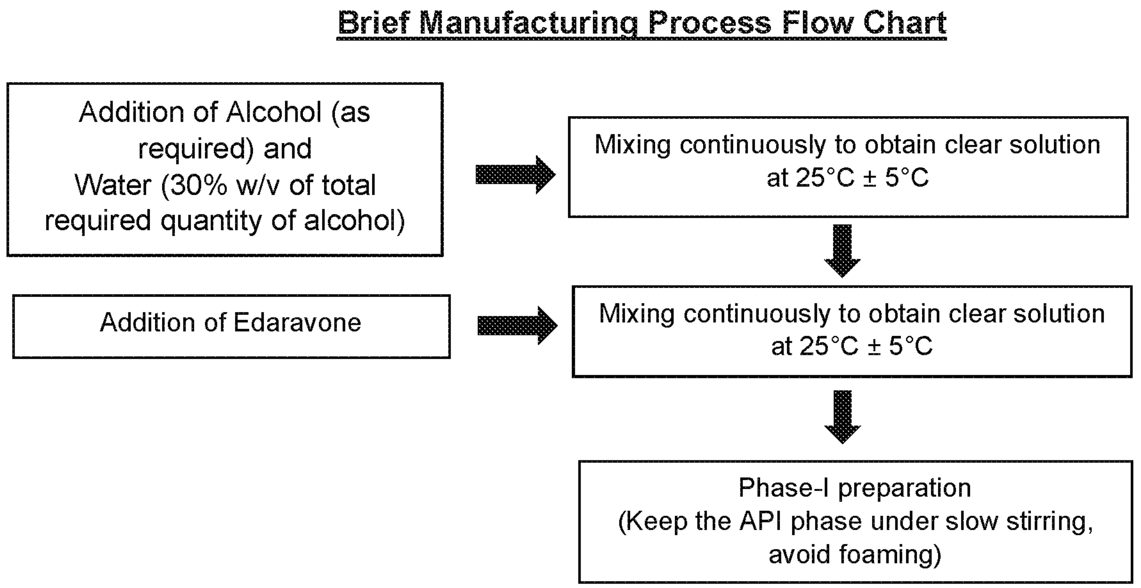
FIG. 1: Preparation of API Phase

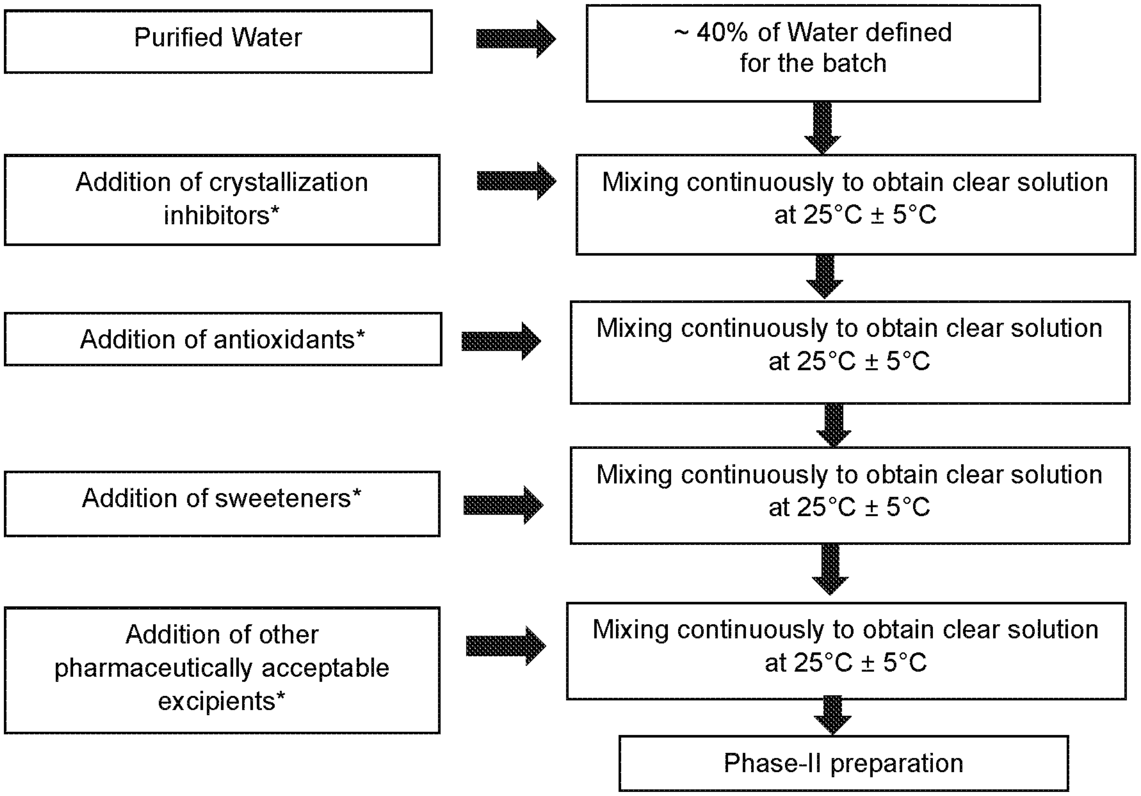
*The order in which excipients are added is not strictly sequential.
FIG. 2: Preparation of Non-API Phase

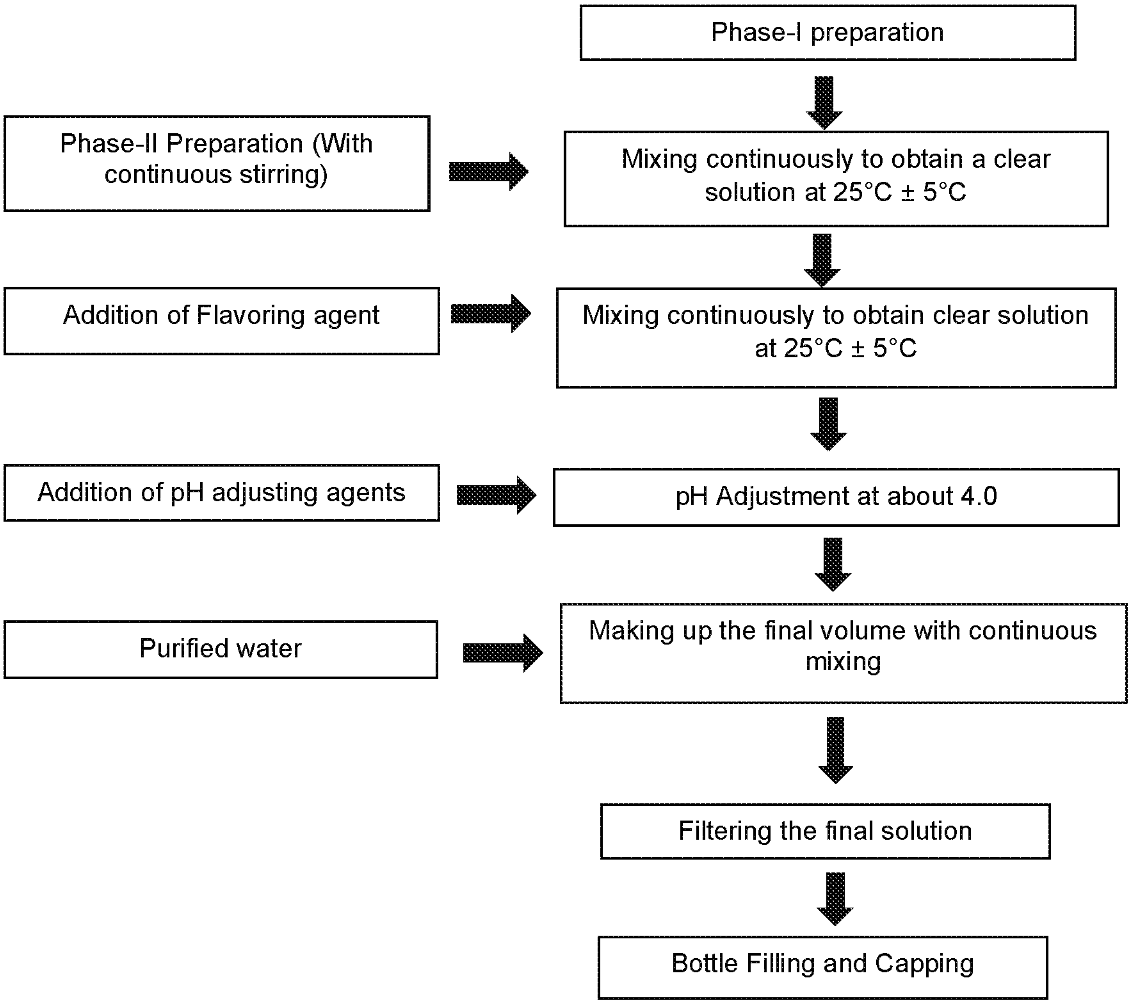
FIG. 3: Preparation of final bulk solution

STABLE PHARMACEUTICAL COMPOSITIONS OF EDARAVONE

CROSS REFERENCE TO RELATED APPLICATIONS

This application is a continuation of application Ser. No. 19/207,816, filed on May 14, 2025, allowed, which is a continuation of application Ser. No. 19/174,002, filed on Apr. 9, 2025, which is a continuation of application Ser. No. 18/340,067, filed on Jun. 23, 2023, now U.S. Pat. No. 12,343,330, which claims the benefit of Indian Provisional Application No. 202341010407, as filed on Feb. 16, 2023, the entire contents of which are incorporated herein.

FIELD OF THE INVENTION

The present invention relates to stable liquid pharmaceutical compositions of edaravone, methods for their administration, processes for their production, and use of these compositions for treatment of diseases treatable by edaravone.

BACKGROUND OF THE INVENTION

Amyotrophic lateral sclerosis (ALS), also known as Lou Gehrig's disease, is a fatal degenerative disease that affects the motor neurons connecting the brain and spinal cord, leading to eventual paralysis and death. Edaravone is an antioxidant that works by preventing oxidative stress induced motor neuron death; and also, by inhibiting nitration of tyrosine residues in the cerebrospinal fluid thus rendering improved motor functions. Edaravone is thereby indicated as a neuroprotective agent for the treatment of ALS. Chemically, this compound is described as 3-methy-1-phenyl-2-pyrazolin-5-one and is represented by the structural formula (I):

(I)

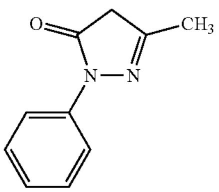

Currently, edaravone is marketed in United States under brand name Radicava® (edaravone injection for intravenous use; 0.3 mg/mL and 0.6 mg/mL) and Radicava ORS® (edaravone oral suspension; 105 mg/5 mL). The recommended dosage for Radicava® is 60 mg administered as an intravenous infusion over 60 minutes. On the other hand, 105 mg (5 mL) of Radicava ORS® is taken orally or via feeding tube in the morning after overnight fasting.

Intravenous (IV) administration is recognized for its precise and comprehensive medication delivery; however, it is also considered a less desirable route of administration due to the added responsibilities it imposes on patients, their families, and healthcare providers. This is primarily due to the frequent need for injections and the requirement for repeated hospital visits and/or caregiver assistance, which can be burdensome. Edaravone in the form of an intravenous infusion also carry similar challenges during administration. Hence, in order to facilitate self-administration and to improve patient compliance, oral route is the most convenient way to administer edaravone for the treatment of ALS.

Dysphagia (difficulty in swallowing) is one of the symptoms of ALS. In addition to deleteriously affecting nutrition intake, dysphagia can also seriously affect the administration of beneficial medications. Solid forms of edaravone, for instance, are not user-friendly for individuals with this condition. Consequently, such patients may delay taking medication or skip the medication entirely, and thus clinicians often seek alternate dosage forms. Furthermore, in advanced dysphagia the oral transfer becomes more difficult because of impaired tongue movement. In such cases, enteral and parenteral routes become vital for delivering both nutrition as well as medication. Hence, dosage forms which are capable of administering drugs to patients with ALS even via an enteral tube should be considered. Liquid formulations, such as solutions or suspensions, effectively fulfill this purpose with ease.

For developing a robust liquid formulation, solubility and stability are the two key factors to be considered. Edaravone is a lipophilic molecule having poor oral bioavailability ($F_{abs}$=5.23%). Such low oral bioavailability is attributed to several factors, including poor solubility, low permeability across the gastrointestinal (GI) tract, and extensive glucuronidation during phase II metabolism. These characteristics in turn classify edaravone as a BCS Class II molecule. The major hurdle to the development of an aqueous liquid formulation of edaravone is its low aqueous solubility, which is measured at 1.85 mg/mL. It is also reported that edaravone exhibits poor stability in aqueous solutions due to rapid degradation. In water, edaravone is present as the 'enol form' and as an 'edaravone anion'. The edaravone anion becomes an edaravone radical when the anion donates an electron to oxygen. Thus, the electron reduction by the edaravone anion is the key step in edaravone degradation.

As stated previously, Radicava ORS© is an approved and commercially available liquid dosage form of edaravone, in the form of an oral suspension. Drugs are formulated as suspensions, for many different reasons, but the most common reasons include poor drug solubility and the poor taste resulting from the dissolved drug in solution. However, the problems associated with suspension dosage forms, which includes sedimentation, caking, poor re-dispersibility or particle growth (Ostwald ripening), may result in drug uniformity concerns which in turn may result in under or over dosing of the medication. Thus, there exists a need for developing robust and stable liquid compositions of edaravone, suitable for enteral administration, wherein edaravone remains in solubilized state over an extended period of time under suitable storage conditions.

U.S. patent Ser. No. 10/966,960 ("Treeway") discloses solid, water-dispersible pharmaceutical compositions of edaravone in combination with a water-soluble alkalizing agent. This composition allows for the preparation of an edaravone solution by simply dispersing it in aqueous liquid at the time of dosage administration. As the disclosed formulation is present in the form of solid composition, it provides an advantage of having a long-term room temperature stability over the commercially available oral suspension of edaravone. There still exists a need for developing a stable as well as ready-to-use edaravone preparation such as an oral solution which exhibits better patient compliance as compared to the disclosed and commercially available preparations of edaravone.

International publication no. WO2023006565A1 ("Medichem S.A.") discloses a process for preparing a heat sterilized, aqueous formulation comprising edaravone and bisulfite anions wherein oxygen content of the said formulation is less than 1 ppm. In case of edaravone, it is always desirable to minimize the use of techniques such as heat sterilization (at 121° C.), as it tends to pose instability issues thereby degrading edaravone and thus producing more objectionable impurities. Furthermore, the presence of bisulfite ions may cause allergic-type reactions including anaphylactic symptoms and life-threatening or less severe asthmatic episodes in certain susceptible people. As per Sec. 201.22 of USFDA Code of Federal Regulations, Title 21, prescription drugs containing sulfites requires a "warning" statement in the labelling section. There is also a need to develop more stable and robust edaravone oral solutions with minimal or no use of excipients containing sulfite ions, without compromising on the solubility and stability of the final formulation.

It is desirable to develop a novel, stable, palatable, ready-to-use solution of edaravone suitable for oral administration to human subjects, exhibiting prolonged room temperature solubility and stability without any significant loss of potency. The present invention fulfils such need by developing a stable solution of edaravone which enhances patient compliance and thus serves to achieve an improved standard of patient care.

SUMMARY OF THE INVENTION

The present invention relates to stable liquid pharmaceutical compositions of edaravone or its pharmaceutically acceptable salts thereof, for treatment of diseases treatable by edaravone. The inventive edaravone compositions are advantageously stable, ready-to-use (RTU) and suitable for enteral administration.

The present invention encompasses various enteral administration methods, including but not limited to oral and gastric administration. Gastric administration can be accomplished through the use of a tube inserted through the nasal passage (nasogastric tube) or a tube placed directly into the stomach via the abdomen (percutaneous endoscopic gastrostomy tube; PEG tube).

An aspect of the present invention relates to a stable solution of edaravone, suitable for enteral administration, comprising at least one pharmaceutically acceptable solvent and one or more pharmaceutically acceptable excipients selected from the group comprising of solubility enhancing agents, antioxidants, crystallization inhibitors, stabilizers, preservatives, flavoring agents, sweetening agents, thickening agents and mixtures thereof.

Yet another aspect of the invention relates to a stable solution of edaravone suitable for enteral administration, wherein edaravone is present at a concentration of about 0.05 mg/mL to about 50 mg/mL.

The stable solution of edaravone of the present invention exhibits a pH of about 2.0 to about 7.0, preferably between about 2.5 to about 6.0.

In another aspect, processes for preparing stable solutions of edaravone suitable for enteral administration are provided, wherein the processes comprise solubilizing edaravone in a solvent along with other pharmaceutically acceptable excipients to obtain a stable solution.

In an aspect, a stable solution comprising (i) edaravone, (ii) at least one pharmaceutically acceptable solvent; and (iii) one or more pharmaceutically acceptable excipients; wherein the solution is stable at 25° C./60% RH for at least 3 months.

In an aspect, a pharmaceutical composition comprising (i) edaravone in an amount ranging from about 0.05 mg/mL to about 50 mg/mL; (ii) water in an amount up to about 50% (w/w); (iii) a non-aqueous solvent in an amount ranging from about 10% (w/w) to about 90% (w/w); (iv) a crystal inhibitor in an amount ranging from about 0.5% (w/w) to about 50% (w/w); and (v) an antioxidant in an amount ranging from about 0.05% (w/w) to about 5.0% (w/w); wherein the composition is in the form of an oral solution and wherein the composition is stable for at least 3 months when stored at 25° C./60% RH or at 40° C./75% RH or at 40° C./25% RH.

In another aspect, a pharmaceutical composition comprising (i) edaravone in an amount ranging from about 0.05 mg/mL to about 50 mg/mL; (ii) water in an amount up to about 50% (w/w); (iii) alcohol in an amount ranging from about 10% (w/w) to about 90% (w/w); (iv) a crystal inhibitor in an amount ranging from about 0.5% (w/w) to about 50% (w/w); and (v) an antioxidant in an amount ranging from about 0.05% (w/w) to about 5.0% (w/w); wherein the composition is in the form of an oral solution and wherein the composition is stable for at least 3 months when stored at 25° C./60% RH or at 40° C./75% RH or at 40° C./25% RH.

Another aspect of the present invention relates to a solution of edaravone having extended stability. In an aspect, the present invention relates to stable solution of edaravone, suitable for enteral administration, wherein said solution is stable for at least 6 months when stored at 40° C./75% RH, 40° C./25% RH, 25° C./60% RH or 2-8° C. conditions.

Another aspect relates to methods of treatment of amyotrophic lateral sclerosis; by enterally administering an effective amount of a stable solution of edaravone.

By way of non-limiting examples, exemplary combinations applicable to the embodiments described in this application may include any combination with one or more of the elements described above.

BRIEF DESCRIPTION OF THE DRAWINGS

FIG. 1. Preparation of API phase.

FIG. 2: Preparation of non-API phase.

FIG. 3: Preparation of final bulk solution.

DETAILED DESCRIPTION OF THE INVENTION

Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

The terms "about" when used along with a numerical variable, generally means the value of the variable and all the values of the variable within a measurement or an experimental error (e.g., 95% confidence interval for the mean) or within a specified value (e.g., ±10%) within a broader range.

The term "pharmaceutically acceptable" substances mean those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to edaravone salts which are formed with inorganic or organic acids.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The term "ready-to-use" or "RTU" as used herein, refers to a formulation that does not require constitution or dilution with a prescribed amount of diluent, e.g., water or other suitable diluent, before use by the designated route.

The term "ready-to-dilute" or "RTD" as used herein refers to a formulation that is diluted with a suitable diluent for enteral administration.

The term "ready-to-administer" or "RTA" as used herein, refers to a formulation that does not require any steps or handling or manipulation before administration and can be directly administered orally to the patient.

The terms "dosage", "dose unit" or "dose" as used herein means amount of pharmaceutical formulation comprising therapeutically active agent(s) administered at a time.

By "effective amount" or "therapeutically effective amount" is meant the amount of a drug sufficient to treat, prevent, or ameliorate a condition in a subject or patient. The effective amount of edaravone or pharmaceutically acceptable salt thereof, may be determined and adjusted by a person of ordinary skill to provide the appropriate amount and dosage regimen, e.g., depending upon manner of administration, the age, body weight, sex, and/or general health of the patient.

Within the context of this invention, the term "solution" refers to a mixture of one or more substances uniformly dissolved in a dissolving liquid medium or vehicle or solvent. The solution is preferably homogeneous, in the sense that Active Pharmaceutical Ingredient (API) is essentially uniformly dissolved and distributed in the solution.

The term "alcohol" as used herein refers to "ethanol" in accordance with the Inactive Ingredient Database (IID) of the United States Food and Drug Administration (USFDA).

The term "subject" refers to a human or non-human beings. The terms "patient" and "subject" may be used interchangeably herein.

The terms "stable" and "stability" mean that the evolution of the product with time and/or under specific environmental conditions (i.e., temperature, humidity, etc.) has no significant effects on its quality, safety and/or efficacy for a given time period. It can be measured through formation of degradation products (impurities), variation of pH, appearance (precipitation), microbial growth, and/or color. The term "stable" may indicate physical stability and/or chemical stability.

The term "physically stable" means a solution of edaravone with no visible edaravone crystals and with no tendency to precipitate upon storage under specified conditions, e.g., at 2-8° C., room temperature, 25° C./60% RH, 40° C./25% RH, 40° C./75% RH for a specified time period of at least 1 week, 2 weeks, 1 month, 2 months, 6 months, 1 year or 2 years.

The term "chemically stable" means that no more than about 10% loss of edaravone under typical commercial storage conditions. Preferably, formulations of the present invention will have no more than about 8% loss of edaravone, more preferably, no more than about a 5% loss of edaravone, more preferably, no more than about a 3% loss of edaravone under specified conditions, e.g., at 2-8° C., or at room temperature, or at 25° C./60% RH, 40° C./25% RH, 40° C./75% RH for at least 2 months, for at least 3 months, at least 6 months, at least 9 months, at least 12 months, at least 15 months, at least 18 months, at least 21 months, at least 24 months, at least 30 months and at least 36 months.

In one embodiment, the stable solutions of the present invention are stable over a wide range of temperature, e.g., −20° C. to 40° C. The stable solutions of the present invention may be stored at about 5° C. to about 25° C.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases, storage of a pharmaceutical formulation is under industry acceptable standards and/or standards that are mandated by regulatory agencies, such as USFDA.

The term "degradation product," as used herein, refers to an unwanted chemical or impurity (including, but not limited to known or unknown related substances) that can develop during the manufacturing, transportation, and/or storage of drug products and can affect the efficacy of pharmaceutical products. It can form in response to changes in light, temperature, pH, and humidity, or due to inherent characteristics of active ingredient, such as their reaction with excipients or on contact with the packaging.

As used herein, "prolonged duration" refers to the holding of a composition under controlled or uncontrolled conditions for a period of more than 30 days.

As used herein, "significant loss of potency" means more than a 10% loss of edaravone under typical commercial storage conditions.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

The expression "bioequivalent" or "bioequivalence" is a term of art and is intended to be defined in accordance with Approved Drug Products with Therapeutic Equivalence Evaluations, 41st Edition, which is published by the U.S. Department of Health and Human Services, and is commonly known as the "Orange Book". Generally, bioequivalence can be defined as the absence of significant difference in the rate and extent to which the active ingredient or active moiety in pharmaceutical equivalents or pharmaceutical alternatives becomes available at the site of drug action when administered at the same molar dose under similar conditions in an appropriately designed study. Bioequivalence of different formulations of the same drug substance involves equivalence with respect to the rate and extent of drug absorption. The pharmacokinetic characteristics of the concentration-time curve, such as the maximum observed plasma concentration (Cmax), the time to reach C max, and the area under the plasma concentration versus time curve (AUC), are examined by statistical procedures which are well-established in the field of pharmacokinetics. Two formulations whose rate and extent of absorption differ by −20%/+25% or less are generally considered to be bioequivalent.

The inventive pharmaceutical compositions described herein are provided in the form of a solution. The modes of enteral administration that may be employed in the present invention include, but not limited to, oral and gastric administration. The enterally acceptable diluents used for oral or gastric administration may comprise water, water for injection, saline, half normal saline, dextrose solution (5%), alcohol, glycerin, polyol (for example, propylene glycol, and polyethylene glycol, and the like), dimethylacetamide, N-methyl-pyrrolidone, dimethyl sulfoxide, ringer's solution, isotonic sodium chloride solution, or suitable mixtures thereof. According to the present invention, the compositions may be provided in a kit form along with a enterally acceptable diluent. The pharmaceutical compositions of the invention may be formulated according to conventional pharmaceutical practice and can be administered in any conventional manner. It will be readily appreciated by those skilled in the art how to administer compositions of the present invention to a human subject.

In one aspect, pharmaceutical composition of the present invention comprises edaravone, wherein the concentration of edaravone ranges from about 0.05 mg/mL to about 50 mg/mL. The present application relates to stable solutions of edaravone, wherein edaravone is present at a concentration of about 5 mg/mL or more.

In a preferred embodiment, concentration of edaravone in the inventive composition is about 0.05 mg/mL, about 0.1 mg/mL, about 0.5 mg/mL, about 1 mg/mL, about 3 mg/mL, about 5 mg/mL, about 6 mg/mL, about 7 mg/mL, 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 30 mg/mL, about 35 mg/mL, about 40 mg/mL, about 45 mg/mL or about 50 mg/mL.

Preferably, the liquid pharmaceutical composition will be provided in a dosage form that is suitable for enteral administration, including but not limited to a solution, suspension, syrup, or elixir. The pharmaceutical compositions may be formulated according to conventional pharmaceutical practice.

As used herein the term "edaravone" refers to edaravone free base or its pharmaceutically acceptable salts, solvates or hydrates thereof. In principle, any crystalline form or amorphous form of edaravone may be used for manufacturing inventive pharmaceutical compositions of the present invention.

In an embodiment, the present invention provides stable liquid pharmaceutical compositions suitable for enteral administration, wherein the composition comprises (i) edaravone, (ii) at least one pharmaceutically acceptable solvent, and (iii) one or more pharmaceutically acceptable excipients.

In an embodiment, the present invention provides stable liquid pharmaceutical compositions suitable for enteral administration, wherein the composition comprises (i) edaravone, (ii) at least one pharmaceutically acceptable non-aqueous solvent, and (iii) one or more pharmaceutically acceptable excipients.

In an embodiment, the present invention provides methods of treatment of amyotrophic lateral sclerosis, by enterally administering to a subject from about 0.5 mg/mL to about 50 mg/mL of stable solution comprising edaravone, wherein the solution comprises (i) edaravone, (ii) at least one pharmaceutically acceptable solvent, and (iii) one or more pharmaceutically acceptable excipients.

In an embodiment, the present invention provides stable pharmaceutical compositions suitable for enteral administration, wherein the composition comprises (i) edaravone (ii) at least one pharmaceutically acceptable solvent, and (iii) one or more pharmaceutically acceptable excipients, wherein the composition is in the form of a solution.

In another embodiment, the present invention provides stable pharmaceutical compositions suitable for enteral administration, wherein the composition comprises (i) edaravone, and (ii) one or more pharmaceutically acceptable excipients, wherein the composition is not in the form of a powder or a granulate.

In yet another embodiment, the present invention provides stable pharmaceutical compositions suitable for enteral administration, wherein the composition comprises (i) edaravone, and (ii) one or more pharmaceutically acceptable excipients, wherein the composition is not in the form of a powder for solution.

In yet another embodiment, the present invention provides stable pharmaceutical compositions suitable for oral administration, wherein the composition comprises (i) edaravone, and (ii) one or more pharmaceutically acceptable excipients, wherein the composition is not in the form of a powder for oral solution.

In yet another embodiment, the present invention provides stable pharmaceutical compositions suitable for oral administration, wherein the composition comprises (i) edaravone (ii) at least one pharmaceutically acceptable solvent and (iii) one or more pharmaceutically acceptable excipients, wherein the composition is not in the form of an oral suspension.

In yet another embodiment, the present invention provides stable pharmaceutical compositions suitable for oral administration, wherein the composition comprises (i) edaravone, and (ii) one or more pharmaceutically acceptable excipients, wherein the composition is not in the form of a powder for oral suspension.

In yet another embodiment, the present invention provides stable pharmaceutical compositions suitable for oral administration, wherein the composition comprises (i) edaravone, (ii) at least one pharmaceutically acceptable solvent, and (iii) one or more pharmaceutically acceptable excipients, wherein the composition is a palatable oral solution.

The terms "solvent" or "pharmaceutically acceptable solvent" or "vehicle" or "pharmaceutically acceptable vehicle" as used herein, is any liquid medium used for dilution or dissolution of enteral formulations, such as water, aqueous organic solvents, non-aqueous organic solvents and other liquids described herein or used in the pharmaceutical and/or food industry. The solvent of the present invention is selected from water, alcohol, propylene glycol, polyethylene glycol, glycerin, dimethylacetamide, N-methyl-pyrrolidone, dimethyl sulfoxide, or their mixtures thereof. Preferably, water, purified water, alcohol, glycerin and propylene glycol are used as liquid vehicles. The non-aqueous solvent may comprise alcohol, glycerin, propylene glycol, polyethylene glycol, N-methyl-pyrrolidone, dimethyl sulfoxide, or mixtures thereof. In a preferred embodiment, the concentration of these pharmaceutically acceptable solvents in the inventive composition ranges from about 5% to about 90%, preferably about 10% to about 70%, more preferably about 15% to about 60%, based on total weight of the composition.

In one embodiment, the present invention provides a stable solution, suitable for enteral administration, comprising (i) edaravone; (ii) at least one pharmaceutically acceptable solvent; and (iii) one or more pharmaceutically acceptable excipients selected from the group consisting of solubility enhancing agents, cosolvents, antioxidants, crystallization inhibitors, pH adjusting agent, buffering agents, stabilizers, preservatives, flavoring agents, sweetening agents, and mixtures thereof.

In another embodiment, the present invention provides a stable solution, suitable for oral administration, comprising (i) edaravone; (ii) at least one pharmaceutically acceptable solvent; and (iii) one or more pharmaceutically acceptable excipients selected from the group consisting of solubility enhancing agents, cosolvents, antioxidants, crystallization inhibitors, pH adjusting agent, buffering agents, stabilizers, preservatives, flavoring agents, sweetening agents, and mixtures thereof.

In another embodiment, the present invention provides a stable solution, suitable for oral administration, comprising (i) edaravone; (ii) at least one pharmaceutically acceptable solvent; and (iii) one or more pharmaceutically acceptable excipients selected from the group comprising solubility enhancing agents, cosolvents, antioxidants, crystallization inhibitors, pH adjusting agent, buffering agents, stabilizers, preservatives, flavoring agents, sweetening agents, and mixtures thereof.

In another embodiment, the present invention provides a stable solution, suitable for oral administration, comprising (i) edaravone; (ii) at least one pharmaceutically acceptable non-aqueous solvent; and (iii) one or more pharmaceutically acceptable excipients selected from the group comprising solubility enhancing agents, cosolvents, antioxidants, crystallization inhibitors, pH adjusting agent, buffering agents, stabilizers, preservatives, flavoring agents, sweetening agents, and mixtures thereof.

In yet another embodiment, the present invention provides a stable solution, suitable for gastric administration comprising (i) edaravone; (ii) at least one pharmaceutically acceptable solvent; and (iii) one or more pharmaceutically acceptable excipients selected from the group consisting of solubility enhancing agents, cosolvents, antioxidants, crystallization inhibitors, pH adjusting agent, buffering agents, stabilizers, preservatives, flavoring agents, sweetening agents, and mixtures thereof.

In one embodiment, the present invention provides a stable solution, suitable for enteral administration, consisting essentially of (i) edaravone; (ii) at least one pharmaceutically acceptable solvent; and (iii) one or more pharmaceutically acceptable excipients selected from the group consisting of solubility enhancing agents, cosolvents, antioxidants, crystallization inhibitors, pH adjusting agent, buffering agents, stabilizers, preservatives, flavoring agents, sweetening agents, and mixtures thereof.

In another embodiment, the present invention provides a stable solution, suitable for enteral administration, consisting of (i) edaravone; (ii) at least one pharmaceutically acceptable solvent; and (iii) one or more pharmaceutically acceptable excipients selected from the group consisting of solubility enhancing agents, cosolvents, antioxidants, crystallization inhibitors, pH adjusting agent, buffering agents, stabilizers, preservatives, flavoring agents, sweetening agents, and mixtures thereof.

In yet another embodiment, the present invention provides a stable solution comprising (i) edaravone; (ii) alcohol; (iii) water; and (iv) one or more pharmaceutically acceptable excipients, wherein the quantity of water in the solution is in an amount up to about 50% w/v, based on total weight of the solution. In yet another embodiment, the present invention provides a stable solution comprising (i) edaravone; (ii) alcohol; (iii) water; and (iv) one or more pharmaceutically acceptable excipients, wherein the quantity of water in the solution is in an amount up to about 1% w/v, up to about 5% w/v, up to about 10% w/v, up to about 15% w/v, up to about 20% w/v, up to about 25% w/v, up to about 30% w/v, up to about 35% w/v, up to about 40% w/v, up to about 45% w/v, up to about 50% w/v, up to about 55% w/v, up to about 60% w/v, up to about 65% w/v, up to about 70% w/v, up to about 75% w/v, up to about 80% w/v, based on total weight of the solution.

In another embodiment, the present invention provides a stable solution comprising (i) edaravone; (ii) non-aqueous solvent; (iii) purified water; and (iv) one or more pharmaceutically acceptable excipients, wherein the quantity of non-aqueous solvent in the solution ranges from about 10% w/v to about 90% w/v, based on total weight of the solution.

In another embodiment, the present invention provides a stable solution comprising (i) edaravone; (ii) alcohol; (iii) purified water; and (iv) one or more pharmaceutically acceptable excipients, wherein the quantity of alcohol in the solution ranges from about 10% w/v to about 90% w/v, based on total weight of the solution.

In yet another embodiment, the present invention provides a stable solution comprising (i) edaravone; (ii) alcohol; (iii) purified water; and (iv) one or more pharmaceutically acceptable excipients, wherein the quantity of alcohol in the solution is at least about 10% w/v, at least about 15% w/v, at least about 20% w/v, at least about 25% w/v, at least about 30% w/v, at least about 35% w/v, at least about 40% w/v, at least about 45% w/v, at least about 50% w/v, at least about 55% w/v, at least about 60% w/v, at least about 65% w/v, at least about 70% w/v, at least about 75% w/v, at least about 80% w/v, at least about 85% w/v, at least about 90% w/v, based on total weight of the solution.

In another embodiment, the present invention provides a stable solution comprising (i) edaravone; (ii) alcohol; (iii) purified water; and (iv) one or more pharmaceutically acceptable excipients, wherein the ratio of quantity of alcohol:water (wt %:wt %) in the solution ranges from about 90:10 to about 10:90. In yet another embodiment, the ratio of alcohol:water (wt %:wt %) ranges from about 90:10 to about 10:90, about 80:20 to about 20:80, about 70:30 to about 30:70, about 60:40 to about 40:60 or about 50:50.

The compositions of the present invention may optionally further include an acidifying agent, alkalizing agent, bulking agent, complexing agent, cryoprotectant, chelating agent, density modifier, electrolyte, plasticizer, volatility modifier, viscosity modifier, antifoaming agent, coloring agent and any other excipients known by those of ordinary skill in the art for use in pharmaceutical compositions.

Edaravone is a poorly water-soluble compound. A solubility enhancing agent is a compound that enhance(s) the solubility of edaravone. Suitable solubility enhancing agents include one or more solvents, oils, surfactants, hydrophilic polymers, polyhydric alcohols, cyclodextrins or mixtures thereof. In a preferred embodiment, concentration of the solubility enhancing agent ranges from about 0.1% to about 90%, based on total weight of the composition.

The inventive compositions as described herein may comprise certain solvents as solubility enhancing agents. Such solvents are used for dissolving active or pharmaceutical excipients other than active ingredient. The non-aqueous solvent may comprise alcohol, glycerin, propylene glycol, polyethylene glycol, N-methyl-pyrrolidone, dimethyl sulfoxide, or mixtures thereof. In a preferred embodiment, the concentration of these solvents ranges from about 1% to about 80%, based on total weight of the composition.

The term "oil" as used herein may function as non-aqueous solvent or solubility enhancing agent, where the function of oil particularly depends on the amount of oil used in inventive compositions as described herein. More specifically, oils may include, for example and without limitation, medium-chain fatty acid, medium-chain fatty acid esters of glycerol (e.g. mono, di or triglyceride), medium-chain fatty acid esters of polyethylene glycol, medium-chain fatty acid esters of propylene glycol, long-chain fatty acid, long-chain fatty acid esters of glycerol (e.g. mono, di or triglyceride), long-chain fatty acid esters of polyethylene glycol, long-chain fatty acid esters of propylene glycol or combinations thereof. In a preferred embodiment, concentration of oil ranges from about 1% to about 80%, based on total weight of the composition.

Suitable surfactants used in the present invention may be ionic or non-ionic surface-active agents. Suitable ionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate; quaternary ammonium compounds such as benzalkonium chloride, benzethonium chloride, cetrimonium bromide, stearyl dimethylbenzyl ammonium chloride, polyoxyethylene. In a preferred embodiment, the concentration of ionic surfactant ranges from about 0.05% to about 50%, based on total weight of the composition.

Suitable nonionic surfactants include, but not limited to, glycol stearates such as ethylene glycol monostearate, propylene glycol myristate, glyceryl monostearate, glyceryl stearate, polyglyceryl-4-oleate, sorbitan acylate, sucrose acylate, polyethylene glycol dilaurate, polyethylene glycol monolaurate, polysorbates, polyoxyethylene octylphenylether, polyethylene glycol cetyl ether, polyoxyethylene tridecyl ether, polypropylene glycol butyl ether, stearoyl monoisopropanolamide, polyoxyethylene hydrogenated tallow amide, polyoxyl-ethylated castor oils (Cremophor®), polyoxyethylene esters of 12-hydroxystearic acid (Solutol®) and PEGylated glycerides (Labrasol®). In a preferred embodiment, the concentration of non-ionic surfactant ranges from about 0.05% to about 50%, based on total weight of the composition.

A hydrophilic polymer as referred to herein is a compound derived by the addition of many smaller units and which has a strong affinity for water. Suitable hydrophilic polymers can be selected from the group consisting of povidone, copovidone, hydroxypropyl cellulose, or hydroxypropyl methylcellulose. In a preferred embodiment, the concentration of hydrophilic polymer ranges from about 0.5% to about 50%, based on total weight of the composition.

A polyhydric alcohol as referred to herein is a compound with more than one hydroxyl group. Non-limiting examples of polyhydric alcohols that can be used are glycerin, propylene glycol, and mannitol. In a preferred embodiment, the concentration of polyhydric alcohol ranges from about 5% to about 80%, based on total weight of the composition.

The cyclodextrins can be selected from the group consisting of α-cyclodextrin, β-cyclodextrin, δ-cyclodextrin, γ-cyclodextrin or their derivatives. In a preferred embodiment, the concentration of cyclodextrins ranges from about 5% to about 80%, based on total weight of the composition.

The table below, illustrates the best possible solubilizing agents that are utilized in the present invention.

TABLE 1

Solubility enhancing agents for edaravone

| Solubility enhancing agents | Solubility mg/gm* |
|---|---|
| Labrasol ALF (Caprylocaproyl Polyoxyl-8 glycerides) | 25.1 |
| Labrasol ALF + Ethanol (50:50) | 78.8 |
| Capryol 90 (Propylene Glycol Monocaprylate) | 15.8 |
| Capryol 90 + Ethanol (50:50) | 65.0 |
| PEG 300 (polyethylene glycol) | 26.4 |
| PEG 300 + Ethanol (50:50) | 66.3 |
| Peppermint Oil | 37.6 |
| Peppermint Oil + Ethanol (50:50) | 72.8 |
| Castor Oil | 7.9 |
| Castor oil + Ethanol (50:50) | 72.2 |
| Cotton seed oil | 2.1 |
| Peanut oil | 1.7 |
| Labrafil M 2125 (Linoleoyl Polyoxyl-6 glycerides) | 9.10 |
| Kollisolv MCT 70 | 8.61 |
| Imwitor 988 (Ester of caprylic acid and glycerol) | 13.59 |
| Miglyol 812 (Triester of caprylic and capric acid) | 11.26 |
| CCMG 400 LQ (Mixture of caprylocaproyl polyoxylglycerides) | 14.36 |
| Polysorbate 20 | 17.7 |
| Alcohol | 52.27 |
| Labrafil M 1944 (Oleoyl polyoxyl-6 glycerides) | 6.9 |
| Lauroglycol 90 (Propylene glycol monolaurate) | 8.1 |

*Quantity of edaravone dissolved per gram of solubility enhancing agent

The present invention involves the use of a solubility enhancing agent for solubilization of the active ingredient (i.e. edaravone). However, edaravone may crystallize over time resulting in loss of desired properties and shortened shelf life. The present invention uses "crystallization inhibitors" or "crystal growth inhibitors" or "crystal inhibitors" in order to promote the physical stability of edaravone in liquid formulations. The term "crystallization inhibitors" or "crystal growth inhibitors" or "crystal inhibitors" as used herein, inhibits the crystallization of active ingredient thereby making the formulation physically stable for a longer period of time. As crystallization inhibitors, highly dispersed silicon dioxide or macromolecular substances are suitable. As macromolecular substances, for example, polyvinylpyrrolidone (Kollidon®), polyvinyl alcohol, glycerin, gelatin, starch (derivatives), dextrins and dextrans, such as, for example, α-, β- and γ-cyclodextrin, dimethyl-βcyclodextrin and 2-hydroxypropyl-β-cyclodextrin), cellulosic or non-cellulosic polymers such as acacia, alginic acid bentonite, carbomer, carboxymethylcellulose calcium or sodium, cetostearyl alcohol, methyl cellulose, ethylcellulose, gelatin guar gum, hydroxyethylcellulose (HEC), hydroxypropylcellulose (HPC), hydroxypropylmethylcellulose (HPMC), maltodextrin, polyvinyl alcohol, povidone, propylene carbonate, propylene glycol alginate, sodium alginate, sodium starch glycolate, starch tragacanth, and xanthan gum, and any combination thereof, sterols (such as cholesterol) or bile acids (such as cholic acid or lithocholic acid), sugar alcohol selected from erythritol, threitol, arabitol, xylitol, ribitol, mannitol, sorbitol, dulcitol, iditol, isomalt, maltitol, lactitol, polyglycitol or combinations thereof. In a preferred embodiment, the concentration of crystallization inhibitors ranges from about 0.5% to about 50%, based on total weight of the composition.

In an embodiment, the present invention provides a stable solution for oral administration comprising (i) edaravone; (ii) at least one pharmaceutically acceptable solvent; (iii) crystallization inhibitor and (iv) one or more pharmaceutically acceptable excipients.

In an embodiment, the present invention provides a stable solution for oral administration comprising (i) edaravone; (ii) at least one pharmaceutically acceptable non-aqueous solvent; (iii) crystallization inhibitor and (iv) one or more pharmaceutically acceptable excipients.

In another embodiment, the present invention provides a stable solution for oral administration comprising (i) edaravone; (ii) alcohol; (iii) purified water; (iv) sorbitol and (v) one or more pharmaceutically acceptable excipients.

In yet another embodiment, the present invention provides a stable solution for oral administration comprising (i) edaravone; (ii) alcohol; (iii) purified water; (iv) xylitol and (v) one or more pharmaceutically acceptable excipients.

The pharmaceutical composition of the present invention may contain a "stability enhancing agent" or "stabilizer". The terms "stability enhancing agent" or "stabilizer" as used herein inhibits, prevents, slows down, or reduces the degradation of edaravone. More specifically, stability enhancing agents include amino acids such as glycine, alanine, glutamate, sodium glutamate, L-arginine, lysine, L-cysteine or methionine; sodium chloride or sodium sulfate salts; ethylenediaminetetraacetic acid (EDTA), metal ions such as zinc, magnesium and calcium or mixtures thereof, natural or synthetic gums such as acacia, alginic acid bentonite, gelatin guar gum, alginate, sodium alginate, starch tragacanth, and xanthan gum, and any combination thereof, cellulosic derivatives such as carboxy methyl cellulose, ethyl cellulose, hydroxyethyl cellulose, hydroxyl propyl cellulose, hydroxyl propyl methylcellulose, methyl cellulose, polyanionic cellulose; cyclodextrins; sugars; sugar alcohols; monosaccharides, disaccharides or polysaccharides or combinations thereof. The concentration of stabilizer ranges from about 0.001% to about 50%, based on total weight of the composition.

The pharmaceutical compositions of the present invention may additionally contain an anti-oxidant. The term "antioxidant" as used herein, refers to an agent which inhibits oxidation and thus is used to prevent the deterioration of preparations by the oxidative process. Such compounds include by way of example and without limitation, sodium bisulfate, ascorbic acid, ascorbyl palmitate, glycine, L-cysteine hydrochloride, L-methionine, butylated hydroxy anisole, butylated hydroxytoluene, hydro phosphorous acid, monothioglycerol, propyl gallate, glutathione, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite, alpha-tocopherol and others known to those of ordinary skill in the art. The concentration of anti-oxidant in the present invention ranges from about 0.001% to about 10%, preferably about 0.01% to about 5.0%, more preferably about 0.05% to about 1.0%, based on total weight of the composition.

In one embodiment, the present invention provides a stable solution for oral administration comprising (i) edaravone; (ii) at least one pharmaceutically acceptable solvent; (iii) one or more antioxidants, and (iv) one or more pharmaceutically acceptable excipients.

In one embodiment, the present invention provides a stable solution for oral administration comprising (i) edaravone; (ii) at least one pharmaceutically acceptable solvent; and (iii) one or more pharmaceutically acceptable excipients, wherein the solution is free of an antioxidant.

In one embodiment, the present invention provides a stable solution for oral administration comprising (i) edaravone; (ii) at least one pharmaceutically acceptable solvent; (iii) one or more antioxidants, and (iv) one or more pharmaceutically acceptable excipients, wherein the solution is free of L-cysteine as an antioxidant.

In another embodiment, the present invention provides a stable solution for oral administration comprising (i) edaravone; (ii) at least one pharmaceutically acceptable solvent; (iii) one or more antioxidants, and (iv) one or more pharmaceutically acceptable excipients, wherein the solution is free of sulfites.

The pH of the inventive composition ranges from about 2 to about 7. In some embodiments, pH of the composition is preferably between about 2.5 to about 6.0, more preferably between about 3.0 to about 5.5. The pharmaceutical compositions of the present invention may contain a buffer, to resist change in pH upon dilution or addition of acid or alkali. Such compounds include, by way of example and without limitation, sodium dihydrogen phosphate monohydrate, disodium hydrogen phosphate anhydrous, citric acid, ascorbic acid, acetic acid, sodium acetate, adipic acid, benzoic acid, sodium benzoate, sodium citrate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium ascorbate anhydrous, sodium ascorbate monohydrate, sodium tartrate and others known to those of ordinary skill in the art. The concentration of buffer in the present invention ranges from about 0.001% to about 10%, based on total weight of the composition.

The pH of the composition can be adjusted with any combination of acidic and/or basic pH adjusting agents known in the art. Acidic materials include organic acids and inorganic acids, in particular, monocarboxylic acids, dicarboxylic acids, and tricarboxylic acids, for example, acetic acid, citric acid, tartaric acid, alpha-hydroxy acids, beta-hydroxy acids, salicylic acid, lactic acid, malic acid, glycolic acid, amino acids and natural fruit acids, or inorganic acids, for example, hydrochloric acid, nitric acid, sulfuric acid, sulfamic acid, phosphoric acid, and combinations thereof. Basic materials include inorganic and organic bases, and combinations thereof. Examples of inorganic bases include but are not limited to the alkali metal hydroxides (especially sodium, potassium, and ammonium), and alkali metal salts such as sodium borate (borax), sodium phosphate, sodium pyrophosphate, and the like; and mixtures thereof. Examples of organic bases include triethanolamine (TEA), diisopropanolamine, triisopropanolamine, aminomethyl propanol, dodecylamine, cocamine, oleamine, morpholine, triamylamine, triethylamine, tetrakis (hydroxypropyl) ethylenediamine, L-arginine, aminomethyl propanol, tromethamine (2-amino 2-hydroxymethyl-1,3-propanediol), and PEG-15 cocamine. Such pH adjusters may be present at a concentration that ranges from about 0.001% to about 20%, based on total weight of the composition.

In one embodiment, the present invention provides a stable solution for oral administration comprising (i) edaravone; (ii) at least one pharmaceutically acceptable solvent; (iii) one or more pH adjusting agents, and (iv) one or more pharmaceutically acceptable excipients.

In one embodiment, the present invention provides a stable solution for oral administration comprising (i) edaravone; (ii) at least one pharmaceutically acceptable solvent; (iii) one or more pH adjusting agents, and (iv) one or more pharmaceutically acceptable excipients, wherein the solution has a pH in the range of about 2.0 to about 7.0, preferably between about 3.0 to about 6.0.

In one embodiment, the present invention provides a stable solution for oral administration comprising (i) edaravone; (ii) at least one pharmaceutically acceptable solvent; and (iii) one or more pharmaceutically acceptable excipients wherein the said solution is free of pH adjusting agents or buffering agents.

In addition to stabilizing pharmaceutical preparations against chemical and physical degradation, liquid preparations, especially multi-dose preparations, must usually be protected from microbial contamination. In one embodiment, pharmaceutical composition of the present invention may optionally comprise a preservative selected from the group consisting of benzoic acid and the sodium or potassium salts thereof, isopropanol, butyl alcohol, benzalkonium chloride, benzethonium chloride, benzyl alcohol, butylparaben, cetylpyridinium chloride, chlorobutanol, chlorocresol, cresol, dehydroacetic acid, ethylparaben, ethylparaben sodium, methylparaben, methylparaben sodium, phenol, phenylethyl alcohol, phenylethanol, phenylmercuric acetate, phenylmercuric nitrate, potassium benzoate, potassium sorbate, propylparaben, propylparaben sodium, butylparaben, sodium dehydroacetate, sodium propionate, sodium benzoate, sorbic acid, thimerosal, thymol, or combinations thereof. The concentration of preservative ranges from about 0.001% to about 10%, based on total weight of the composition.

The pharmaceutical compositions of the present invention are optionally preservative-free compositions. The term "preservative-free" means that the present compositions and methods comprise no use of preservatives.

The term "sweetening agents" refers to both bulk (caloric) and intense (non-caloric) sweeteners, which impart sweet taste to the preparation. Examples of sweeteners are acesulfame, alitame, aspartame, cyclamate, saccharin, sucralose, acesulfame potassium or sodium cyclamate, sorbitol, xylitol, magna sweet 110 and mixtures thereof. The concentration of sweetener ranges from about 0.001% to about 10%, based on total weight of the composition The term "flavoring agent," as used herein, refers to an agent or a mixture of agents that adds flavor to a mixture. Flavoring agent is selected from the group consisting of a natural flavor, an artificial flavor, and mixtures thereof. Flavoring agents include, but are not limited to, mint, peppermint, cola, apple, vanilla, grape, orange, menthol, peach, apricot, raspberry, cherry, honey, lemon, coconut, pineapple, strawberry banana, mixed berry, mixed red fruit, Magna sweet 110, and cream flavors and mixture thereof. The concentration of flavoring agent ranges from about 0.001% to about 10%, based on total weight of the composition.

Further, it would be desirable to have a solution of edaravone which is convenient to administer to patients unable to ingest solid or liquid dosage forms. Hence, in such cases, it is desirable that the edaravone solution of the present invention is administered through indwelling tubes, such as nasogastric tubes or other similar tubes.

In a preferred embodiment, the present invention provides a stable solution for oral administration comprising (i) edaravone; (ii) at least one pharmaceutically acceptable solvent; (iii) one or more pharmaceutically acceptable excipients, wherein the solution can be administered through an indwelling tube without clogging, for example, nasogastric or other feeding tubes (jejunal or duodenal) including small bore needle catheter feeding tubes.

In an embodiment, the present invention provides a stable solution comprising (i) edaravone; (ii) at least one pharmaceutically acceptable solvent; (iii) one or more pharmaceutically acceptable excipients, wherein in said composition upon enteral administration exhibits bioequivalence to a commercially available reference i.e. Radicava ORS®, and wherein said bioequivalence is established by at least one of: (i) a confidence interval for mean AUC0-t between about 80% and about 125%; (ii) a confidence interval for mean AUC0-infinity between about 80% and about 125%; (iii) a confidence interval for mean Cmax between about 80% and about 125% or a combination thereof.

In an embodiment, the present invention provides a process for preparation of a stable solution of edaravone for enteral administration, wherein the process comprises solubilizing edaravone in a solvent along with other pharmaceutically acceptable excipients to obtain a stable solution In an embodiment, the pharmaceutical composition of present invention is filled into suitable pharmaceutically acceptable containers selected from the group consisting of bottles, bags and vials.

In an embodiment, the pharmaceutically acceptable container is a bottle, wherein the bottle is selected from group consisting of glass bottle or plastic bottle, wherein glass bottle is selected from group consisting of Type I, II and III borosilicate glass bottles, wherein the glass bottle may be amber color glass bottle or clear glass bottle.

In another embodiment, the pharmaceutically acceptable container is a bottle, wherein the bottle is selected from group consisting of high-density polyethylene (HDPE) bottle, polyethylene terephthalate (PET) and polypropylene (PP), wherein the plastic bottle may be amber color, white opaque or translucent plastic bottle.

In a preferred embodiment, the glass and HDPE bottles will be available in about 30, about 50, about 60, about 100, about 120, about 150, about 250, or about 500 mL fill volumes.

In an embodiment, the pharmaceutical composition of present application was packed in a kit comprising bottle with child resistant cap, dosing syringe, adapter and dosing syringe.

A pharmaceutically inert gas may be bubbled into the solution to drive out oxygen, selected from nitrogen or carbon dioxide. Preferably, the solution was kept under nitrogen or carbon dioxide sparging until dissolved oxygen is less than about 1 ppm in the final solution.

According to another embodiment, the pharmaceutical composition of the present invention, packed in a suitable container, is covered by an overpouch or overwrap, preferably by a light and oxygen protective overpouch that protects the formulations from the impact of light and from the ingress of oxygen and preferably providing another moisture and/or gas barrier, such as, for example, aluminium foil or polypropylene films.

In an embodiment, an oxygen absorber or scavenger, such as, for example, absorbent material, is placed between the inner or primary container and the overwrap or the overpouch. In yet another embodiment, an oxygen indicator is placed, which indicates if oxygen has penetrated the overpouch.

In a preferred embodiment, the present invention provides a stable solution for oral administration comprising (i) edaravone; (ii) at least one pharmaceutically acceptable solvent; (iii) one or more pharmaceutically acceptable excipients, wherein the solution has total oxygen content of not more than about 10 ppm, not more than about 8 ppm, not more than about 6 ppm, not more than about 5 ppm, not more than about 4 ppm, not more than about 3 ppm, not more than about 2 ppm, not more than about 1 ppm or preferably not more than about 0.5 ppm.

Stability:

The term "stable" may indicate physical stability and/or chemical stability. The term "physically stable" means a solution of edaravone with no visible edaravone crystals and with no tendency to precipitate upon storage under specified conditions, e.g., at 2-8° C., room temperature, 25° C./60% RH, 40° C./25% RH, 40° C./75% RH for a specified time period of at least 1 week, 2 weeks, 1 month, 2 months, 6 months, 1 year or 2 years. The term "chemically stable" means that no more than about 10% loss of edaravone under typical commercial storage conditions. Preferably, formulations of the present invention will have no more than about 8% loss of edaravone, more preferably, no more than about a 5% loss of edaravone, more preferably, no more than about a 3% loss of edaravone under specified conditions, e.g., at 2-8° C., or at room temperature, or at 25° C./60% RH, 40° C./25% RH, 40° C./75% RH for at least 2 months, for at least 3 months, at least 6 months, at least 9 months, at least 12 months, at least 15 months, at least 18 months, at least 21 months, at least 24 months, at least 30 months and at least 36 months. In yet another embodiment, the compositions of the present invention, the level of total impurities in the composition is less than about 5% w/w, less than about 3% w/w, less than about 2% w/w, less than about 1% w/w, less than about 0.5% w/w, under typical commercial storage conditions. The composition retains at least about 90% of the potency of edaravone, as determined by HPLC, after storing the composition at 40° C./75% RH or at 40° C./25% RH or at 25° C./60% RH or at room temperature for at least 6 months. In certain aspects, the composition retains at least about 95% of the potency of edaravone, as determined by HPLC, after storing at 2-8° C. for at least twelve months.

In an embodiment, the present invention provides a stable solution comprising (i) edaravone, (ii) at least one pharmaceutically acceptable solvent, (iii) one or more pharmaceutically acceptable excipients, wherein the solution is stable when stored at room temperature conditions for prolonged duration without significant loss of potency.

In an embodiment, the present invention provides a stable solution comprising (i) edaravone, (ii) at least one pharmaceutically acceptable solvent, (iii) one or more pharmaceutically acceptable excipients, wherein the solution is stable for at least 15 days, for at least 1 month, for at least 2 months, or for at least 3 months, or for at least 3 months, or for at least 6 months, or for at least 9 months, or for at least 12 months or for at least 24 months when stored at 25° C./60% RH or 25° C./40% RH.

In an embodiment, the present invention provides a stable solution comprising (i) edaravone, (ii) at least one pharmaceutically acceptable liquid solvent, (iii) one or more pharmaceutically acceptable excipients, wherein the solution is stable for at least 15 days, for at least 1 month, for at least 2 months, or for at least 3 months, or for at least 3 months, or for at least 6 months, or for at least 9 months, or for at least 12 months or for at least 24 months when stored at 40° C./75% RH or 40° C./25% RH.

In an embodiment, the present invention provides a stable solution comprising (i) edaravone, (ii) at least one pharmaceutically acceptable solvent, (iii) one or more pharmaceutically acceptable excipients, wherein the solution is stable for at least 1 month, for at least 3 months, or for at least 6 months, or for at least 12 months, or for at least 18 months, or for at least 24 months, or for at least 36 months when stored at 2-8° C.

In an embodiment, the present invention provides a stable solution comprising (i) edaravone, (ii) at least one pharmaceutically acceptable solvent, (iii) one or more pharmaceutically acceptable excipients, wherein said solution is stable at 2-8° C. for at least 18 months followed by storage at 25° C. or at room temperature for at least 30 days.

Edaravone has known as well as unknown impurities. In particular, known impurities such as oxidation impurity, phenyl hydrazine impurity, dimer impurity, trimer impurity and amine impurity are observed. The following table lists potential impurities of edaravone.

TABLE 2

The potential impurities for Edaravone

| S. No | Impurity Name | Type | Structure | Nature/Source of formation |
|---|---|---|---|---|
| 1. | Oxidation impurity | Degradation | 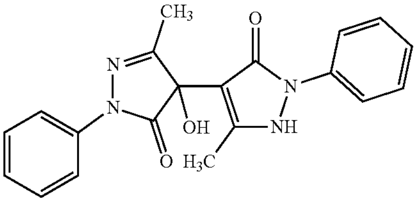 [SMILES: CC1=NN(c2ccccc2)C(=O)C1(O)c1c(C)[nH]n(-c2ccccc2)c1=O] | Base-hydrolysis & Thermal conditions. (Undergoes oxidation once active) |
| 2. | Phenyl hydrazine impurity | Process-related | 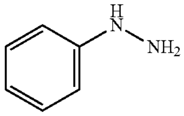 | Presence of oxygen |
| 3. | Amine impurity (Aniline) | Process-related | 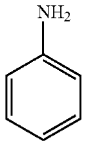 | Presence of oxygen |

TABLE 2-continued

The potential impurities for Edaravone

| S. No | Impurity Name | Type | Structure | Nature/Source of formation |
|---|---|---|---|---|
| 4. | Edaravone Impurity-A [Edaravone Dimer impurity] | Degradation | 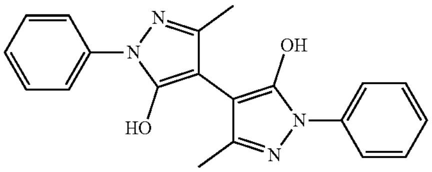 [SMILES: Cc1nn(-c2ccccc2)c(O)c1-c1c(C)nn(-c2ccccc2)c1O] | Thermal/Hydrolysis/ Oxidation/Light |
| 5. | Edaravone Impurity-B [Edaravone Impurity V] | Not known | 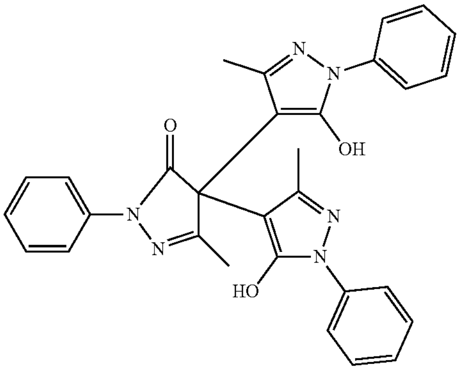 [SMILES: CC1=NN(c2ccccc2)C(=O)C1(c1c(C)nn(-c2ccccc2)c1O)c1c(C)nn(-c2ccccc2)c1O] | Not known |
| 6. | Edaravone Impurity-C [Edaravone Impurity 2] | Not known | 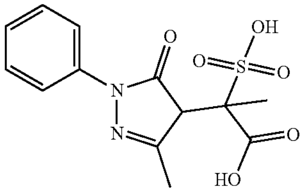 [SMILES: CC1=NN(c2ccccc2)C(=O)C1C(C)(C(=O)O)S(=O)(=O)O] | Not known |
| 7. | Edaravone Impurity-D [Edaravone Impurity P3] | Not known | 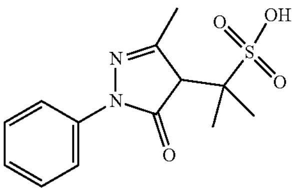 [SMILES: CC1=NN(c2ccccc2)C(=O)C1C(C)(C)S(=O)(=O)O] | Not known |
| 8. | Edaravone Impurity-E [Edaravone Impurity IV] | Not known | 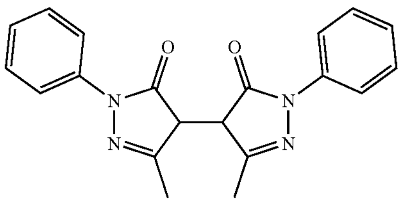 [SMILES: CC1=NN(c2ccccc2)C(=O)C1C1C(=O)N(c2ccccc2)N=C1C] | Not known |

TABLE 2-continued

| The potential impurities for Edaravone | | | | |
|---|---|---|---|---|
| S. No | Impurity Name | Type | Structure | Nature/Source of formation |
| 9. | Edaravone Impurity-F [Edaravone Trimer Impurity] | Not known | 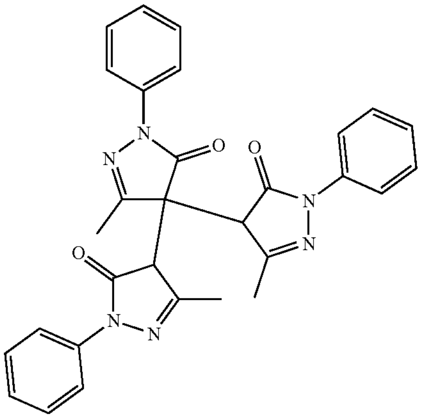 [SMILES: CC1=NN(c2ccccc2)C(=O)C1C1(C2C(=O)N(c3ccccc3)N=C2C)C(=O)N(c2ccccc2)N=C1C] | Thermal/Hydrolysis/ Oxidation/Light |
| 10. | Edaravone Impurity-7 [Edaravone Dimer N Oxide Impurity] | Not known | 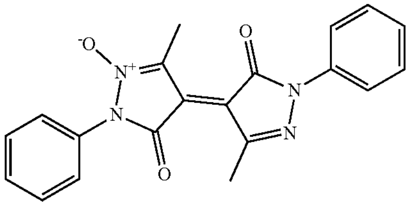 | Not known |

In an embodiment, the present invention provides stable solution, meant for enteral administration, wherein the level of total impurities in the composition is less than about 50% w/w, less than about 30% w/w, less than about 2% w/w, less than about 1% w/w, less than about 0.50% w/w as determined by HPLC.

In another embodiment, the level of any unknown impurities in the inventive composition resulting from the degradation of edaravone is less than about 2% (w/w), less than about 1.5% (w/w), less than about 1% (w/w), less than about 0.5% (w/w), less than about 0.4% (w/w), less than about 0.3% (w/w), less than about 0.2% (w/w), less than about 0.15% (w/w) and less than about 0.10% (w/w) as determined by HPLC.

In yet another embodiment, the level of known impurities in the inventive composition resulting from the degradation of edaravone is less than about 2% (w/w), less than about 1.500 (w/w), less than about 1% (w/w), less than about 0.5% (w/w), less than about 0.4% (w/w), less than about 0.3% (w/w), less than about 0.2% (w/w), less than about 0.15% (w/w) and less than about 0.1% (w/w) as determined by HPLC.

In an embodiment, a stable solution comprising (i) edaravone, (ii) at least one pharmaceutically acceptable solvent; and (iii) one or more pharmaceutically acceptable excipients; wherein the solution is stable at 25° C./60% RH for at least 3 months.

In an embodiment, a pharmaceutical composition comprising (i) edaravone in an amount ranging from about 0.05 mg/mL to about 50 mg/mL; (ii) water in an amount up to about 50% (w/w); (iii) a non-aqueous solvent in an amount ranging from about 10% (w/w) to about 90% (w/w); (iv) a crystal inhibitor in an amount ranging from about 0.5% (w/w) to about 50% (w/w); and (v) an antioxidant in an amount ranging from about 0.05% (w/w) to 5.0% (w/w); wherein the composition is in the form of an oral solution and wherein the composition is stable for at least 3 months when stored at 25° C./60% RH or at 40° C./75% RH or at 40° C./25% RH.

In yet another embodiment, a pharmaceutical composition comprising (i) edaravone in an amount ranging from about 0.05 mg/mL to about 50 mg/mL; (ii) water in an amount up to about 50% (w/w); (iii) alcohol in an amount ranging from about 10% (w/w) to about 90% (w/w); (iv) a crystal inhibitor in an amount ranging from about 0.5% (w/w) to about 50% (w/w); and (v) an antioxidant in an amount ranging from about 0.05% (w/w) to about 5.0% (w/w); wherein the composition is in the form of an oral solution and wherein the composition is stable for at least 3 months when stored at 25° C./60% RH or at 40° C./75% RH or at 40° C./25% RH.

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Edaravone compositions are set forth in Table 3:

TABLE 3

| Composition Details | | | |
|---|---|---|---|
| | | Composition | |
| | | A | B |
| Ingredients | Category | Qty mg/ml | |
| Edaravone | API | 21.0 | 21.0 |
| Sodium Bisulfite | antioxidant | 1.8 | 1.8 |
| L-cysteine HCl hydrate | antioxidant | 2.0 | 2.0 |
| Alcohol | solvent | 400.0 | 350.0 |
| Xanthan Gum | crystal growth inhibitors | 2.0 | 2.0 |
| Hydroxypropyl methylcellulose (HPMC E5) | crystal growth inhibitors | 6.0 | 10.0 |
| Xylitol | crystal growth inhibitors | 60.0 | — |
| Tartaric Acid | Antioxidant | 1.00 | — |
| Sucralose | sweetener | 1.20 | 1.20 |
| Grape Flavor | Flavor | 1.20 | — |
| Purified water | solvent | Qs to 1 ml | Qs to 1 ml |

Brief manufacturing process flow charts are as described in FIGS. 1, 2 and 3.

Freeze thaw cycle (FTC) study: Above compositions were subjected to FTC study, wherein 3 cycles of FTC were carried out at −20° C. and Room Temperature for 24 hours each.

TABLE 4

| Initial and stability analysis data of Composition A | | | | | |
|---|---|---|---|---|---|
| Composition A | | | | | |
| Initial Assay | | 96.6 | | | |
| 3 cycle FTC Assay | | 98.3 | | | |
| Assay 2-8 °C(12 Days) | | 97.9 | | | |
| Related Substance | Initial | 1 W 40 °C/75% RH | 2 W 40 °C/75% RH | 1M 2-8 °C | 1M 25 °C/60% RH |
| Phenyl Hydrazine | ND | ND | ND | ND | ND |
| Amine Impurity | 0.01 | 0.01 | ND | ND | ND |
| Oxidation Impurity | 0.01 | 0.02 | 0.005 | ND | ND |
| Single Max | 0.06 | 0.21 | 0.199 | 0.08 | 0.12 |
| Total | 0.21 | 0.71 | 0.769 | 0.21 | 0.51 |

TABLE 5

| Initial and stability analysis data of Composition B<br>Composition B | | | |
|---|---|---|---|
| | Initial | 1M 25 °C/60% RH | 1M 2-8 °C |
| Assay | 99.9 | 98.4 | 99.2 |
| Related Substances | | | |
| Oxidation Impurity | ND | 0.01 | ND |
| Single Max | 0.05 | 0.26 | 0.05 |
| Total | 0.12 | 0.99 | 0.11 |

Example 2: Role of Antioxidant

TABLE 6

| Composition Details | | | | | |
|---|---|---|---|---|---|
| Composition | Category | C | D | E | O |
| Edaravone | API | 21.0 | 21.0 | 21.0 | 21.0 |
| Sodium Bisulfite | antioxidant | 1.8 | 1.8 | — | — |
| L-cysteine HCl | antioxidant | 2.0 | 7.0 | — | 0.5 |
| Alcohol | solvent | 400.0 | 400.0 | 400.0 | 400.0 |
| Xanthan Gum | crystal growth inhibitors | 1.0 | 1.0 | 1.0 | 1.0 |
| HPMC | crystal growth inhibitors | 10.0 | 10.0 | 10.0 | — |
| Polyvinyl alcohol | crystal growth inhibitors | — | — | — | 1.0 |
| Xylitol | crystal growth inhibitors/sweetener | 60.0 | 60.0 | 60.0 | — |
| Sorbitol | crystal growth inhibitors//sweetener | — | — | — | 100.0 |
| Sucralose | sweetener | 3.0 | 3.0 | 3.0 | — |
| Purified water | solvent | Qs to 1 ml | Qs to 1 ml | Qs to 1 ml | Qs to 1 ml |

Brief manufacturing process flow charts are as described in FIGS. 1, 2 and 3.

TABLE 6

| Initial and stability analysis data of Composition C and D | | | | | | | | |
|---|---|---|---|---|---|---|---|---|
| | Composition | | | | | | | |
| | C | | | | D | | | |
| | Condition | | | | | | | |
| | | 1 W | 1M | | | 1 W | 1M | |
| | Initial | 40 °C/ 75% RH | 25 °C/ 60% RH | 2°-8 °C | Initial | 40 °C/ 75% RH | 25 °C/ 60% RH | 2°-8 °C |
| Edaravone Assay | 97.7 | Not done | 96.4 | 97.7 | Not done | Not done | 91.5 | 97.8 |
| Oxidation Impurity | ND | 0.01 | ND | ND | ND | 0.02 | ND | ND |

TABLE 6-continued

Initial and stability analysis data of Composition C and D

| | Composition C | | | | Composition D | | | |
|---|---|---|---|---|---|---|---|---|
| | Condition | | | | | | | |
| | | 1 W | 1M | | | 1 W | 1M | |
| | Initial | 40 °C/ 75% RH | 25 °C/ 60% RH | 2°-8 °C | Initial | 40 °C/ 75% RH | 25 °C/ 60% RH | 2°-8 °C |
| Single Max unknown impurity | 0.05 | 0.35 | 0.26 | 0.05 | 0.13 | 0.63 | 2.27 | 0.3 |
| Total | 0.13 | 1.65 | 1.15 | 0.11 | 0.26 | 4.86 | 5.25 | 1.13 |

TABLE 7

Initial and stability analysis data of Composition E

| | Composition E | | | |
|---|---|---|---|---|
| Condition | Initial | 2M 2°-8 °C | 2M 25 °C/ 60% RH | 1M 40 °C/ 75% RH |
| Edaravone Assay | 97.0 | 97.90 | 97.60 | Not Done |
| Oxidation Impurity | 0.02 | 0.05 | 0.14 | 0.09 |
| Trimer F Impurity | — | 0.07 | 0.28 | — |
| Dimer Impurity | — | ND | 0.01 | — |
| Single Max Unknown Impurity | 0.05 | 0.03 | 0.06 | 0.96 |
| Total Impurities | 0.12 | 0.16 | 0.56 | 1.42 |

TABLE 8

Initial and stability analysis data of Composition O
Composition O

| | Condition | | | | | |
|---|---|---|---|---|---|---|
| | Initial | 2 W 40 °C/ 75% RH | 2M 2°-8 °C | 3M 2°-8 °C | 2M 25 °C/ 60% RH | 3M 25 °C/ 60% RH |
| Edaravone Assay | 97.5 | Not performed | | | | |
| Oxidation Impurity | ND | 0.01 | ND | 0.01 | ND | 0.02 |
| Trimer F Impurity | — | — | 0.07 | 0.04 | 0.09 | 0.07 |
| Dimer Impurity | — | — | ND | ND | ND | 0.01 |
| Single Max Unknown Impurity | 0.05 | 0.09 | 0.02 | 0.02 | 0.06 | 0.04 |
| Total Impurities | 0.09 | 0.29 | 0.12 | 0.17 | 0.29 | 0.35 |

Example 3: Role of Crystallization Inhibitors

TABLE 9

Trials with sorbitol and xylitol as crystallization inhibitors

| Composition | Category | F | G | H | I |
|---|---|---|---|---|---|
| Edaravone | API | 21.0 | 21.0 | 21.0 | 21.0 |
| Sodium Bisulfite | antioxidant | 1.0 | 1.0 | 1.00 | 1.80 |
| L-cysteine HCl hydrate | antioxidant | 0.5 | 0.5 | — | — |
| Alcohol | solvent | 400.0 | 400.0 | 400.0 | 400.0 |
| Xanthan Gum | crystal growth inhibitors | 1.0 | 1.0 | — | — |

TABLE 9-continued

Trials with sorbitol and xylitol as crystallization inhibitors

| Composition | Category | F | G | H | I |
|---|---|---|---|---|---|
| HPMC | crystal growth inhibitors | — | — | — | 10.0 |
| polyvinyl alcohol (PVA) | crystal growth inhibitors | 1.0 | 1.0 | — | — |
| Sorbitol 70/70 | sweetener/ crystal growth inhibitors | 100.0 | 200.0 | 400.0 | — |
| Xylitol | sweetener/ crystal growth inhibitors | — | — | — | 100.0 |
| Glycerin | crystal growth inhibitors | — | — | — | 60.0 |
| Sucralose | sweetener | — | — | — | 5.0 |
| Purified water | solvent | Qs to 1 ml | Qs to 1 ml | Qs to 1 ml | Qs to 1 ml |

Brief manufacturing process flow charts are as described in FIGS. 1, 2 and 3.

TABLE 10

Initial and stability analysis data of Composition F
Composition F

| Condition | Initial | 1 M 40 °C/ 75% RH | 2M 2- 8 °C | 2M 25 °C/ 60% RH |
|---|---|---|---|---|
| Edaravone Assay | 95.9 | 96.5 | 96.3 | 99.1 |
| Oxidation Impurity | ND | ND | ND | ND |
| Trimer F Impurity | NA | 0.15 | 0.06 | 0.08 |
| Dimer Impurity | NA | 0.01 | ND | ND |
| Single Max Unknown Impurity | 0.05 | 0.12 | 0.02 | 0.02 |
| Total Impurities | 0.1 | 0.67 | 0.1 | 0.19 |

TABLE 11

Initial and stability analysis data of Composition G

| | Composition G | | |
|---|---|---|---|
| Condition | Initial | 1 W 40° C./75% RH | 2 W 40° C./75% RH |
| Oxidation Impurity | ND | ND | ND |
| Single Max Unknown Impurities | 0.05 | 0.05 | 0.07 |

TABLE 11-continued

Initial and stability analysis data of Composition G

| Condition | Initial | Composition G 1 W 40° C./75% RH | 2 W 40° C./75% RH |
|---|---|---|---|
| Total Impurities | 0.1 | 0.15 | 0.22 |
| Edaravone Assay | | — | 100.6 |
| Observation at 40 °C/75% RH | Clear colorless Solution | | |

TABLE 12

Initial and stability analysis data of Composition H

| Condition | Initial | Composition H 1M 25 °C/ 60% RH | 1M 2 °C- 8 °C | 2M 25 °C/ 60% RH | 2M 2 °C- 8 °C |
|---|---|---|---|---|---|
| Edaravone Assay | 101.0 | 100.4 | 100.4 | 99.3 | 99.7 |
| Oxidation Impurity | ND | 0.01 | ND | 0.03 | 0.02 |
| Trimer F Impurity | NA | 0.09 | 0.07 | 0.12 | 007 |
| Dimer Impurity | NA | ND | ND | ND | ND |
| Single Max Unknown Impurity | 0.05 | 0.02 | 0.02 | 0.04 | 0.04 |
| Total Impurities | 0.09 | 0.19 | 0.12 | 0.37 | 0.16 |

TABLE 13

Initial and stability analysis data of Composition I

| Condition | Initial | Composition I 1M 25 °C/ 60% RH | 2M 25 °C/ 60% RH | 1M 2 °C- 8 °C | 2M 2 °C- 8 °C |
|---|---|---|---|---|---|
| Edaravone Assay | 97.3 | 100.6 | 96.10 | 101.2 | 96.60 |
| Oxidation Impurity | ND | ND | 0.02 | ND | 0.02 |
| Trimer F Impurity | NA | 0.09 | 0.16 | 0.07 | 0.07 |
| Dimer Impurity | NA | ND | ND | ND | ND |
| Single Max Unknown Impurities | 0.05 | 0.05 | 0.1 | 0.02 | 0.05 |
| Total Impurities | 0.1 | 0.21 | 0.41 | 0.14 | 0.20 |

Example 4: Edaravone Compositions

TABLE 14

Composition details
Composition J

| Ingredients | Function | mg/ml | % W/W |
|---|---|---|---|
| Edaravone | API | 21.0 | 2.1 |
| Alcohol | Solvent | 400.00 | 40 |
| Xanthan Gum | Crystal Growth Inhibitor | 1.00 | 0.1 |
| Xylitol | Crystal Growth Inhibitor/Sweetener | 100.0 | 10 |
| Sodium Bisulfite | Antioxidant | 1.00 | 0.1 |
| L-cysteine hydrochloride | Antioxidant | 0.50 | 0.05 |
| Glycerin | Crystal Growth Inhibitor | 100.0 | 10 |
| Sucralose | Sweetener | 3.00 | 0.3 |
| Grape Flavor (856.085) | Flavour | 2.00 | 0.2 |
| Anhydrous Citric Acid | pH Modifier | Qs to adjust pH | — |
| Sodium Citrate, Dihydrate | pH Modifier | Qs to adjust pH | — |
| Purified Water | Vehicle | up to 1 mL | 37.15 |

Brief manufacturing process flow charts are as described in FIGS. 1, 2 and 3.

TABLE 15

Initial and stability analysis data of Composition J

| Condition | Initial | Composition J pH 4.00 3M 40 °C/ 75% RH | 3M 2- 8 °C | 3M 25 °C/ 60% RH |
|---|---|---|---|---|
| Assay Edaravone | 99.3 | 97.9 | 98.8 | 100 |
| Oxidation Impurity | 0.02 | 0.01 | 0.02 | 0.02 |
| Trimer F Impurity | 0.07 | 0.28 | 0.04 | 0.07 |
| Dimer Impurity | ND | ND | ND | ND |
| Single Max Unknown impurity | 0.03) | 0.216 | 0.02 | 0.021 |
| Total Impurities | 0.14 | 1.17 | 0.10 | 0.19 |

Example 4: pH Study on Composition pH study was carried out on Composition J, wherein pH of the final solution was adjusted to 3.0, 3.5, 4.0, 4.5 and 5.0. The analytical data is as follows:

TABLE 16

Initial and stability analysis data of Composition K & L

| | Parameters: Composition K, pH 3.00, Condition: Initial | 1M 40 °C/ 75% RH | 2M 2-8 °C | 2M 0 25 °C/ 60% RH | Composition L, pH 3.50: Initial | 1M 40 °C/ 75% RH | 2M 2-8 °C | 2M 25 °C/ 60% RH |
|---|---|---|---|---|---|---|---|---|
| Assay (Edaravone) | 96.1 | 93.9 | 99.3 | 98.2 | 98.7 | 98.8 | 101.2 | 102.1 |
| pH | 3.04 | 3.01 | 3.01 | 3.03 | 3.54 | 3.39 | 3.52 | 3.46 |
| Oxidation Impurity | ND | ND | 0.14 | 0.04 | ND | 0.02 | ND | ND |

TABLE 16-continued

Initial and stability analysis data of Composition K & L

| | Parameters | | | | | | | |
|---|---|---|---|---|---|---|---|---|
| | Composition K | | | | Composition L | | | |
| | pH | | | | | | | |
| | 3.00 | | | | 3.50 | | | |
| | Condition | | | | | | | |
| | Initial | 1M 40 °C/ 75% RH | 2M 2-8 °C | 2M 0 25 °C/ 60% RH | Initial | 1M 40 °C/ 75% RH | 2M 2-8 °C | 2M 25 °C/ 60% RH |
| Trimer F Impurity | 0.07 | 0.2 | 0.12 | 0.13 | 0.07 | 0.14 | 0.07 | 0.11 |
| Dimer Impurity | 0.01 | 0.059 | ND | ND | ND | 0.03 | ND | ND |
| Single Max Unknown impurity | 0.03 | 0.06 | 0.021 | 0.077 | 0.03 | 0.17 | 0.023 | 0.026 |
| Total impurities | 0.15 | 0.7 | 0.34 | 0.50 | 0.15 | 0.73 | 0.14 | 0.25 |

TABLE 17

Initial and stability analysis data of Composition M & N

| | Composition M | | | | Composition N | | | |
|---|---|---|---|---|---|---|---|---|
| | pH | | | | | | | |
| | 4.5 | | | | 5.0 | | | |
| | Condition | | | | | | | |
| | Initial | 1M 40 °C/ 75% RH | 2M 2-8 °C | 2M 25 °C/ 60% RH | Initial | 1M 40 °C/ 75% RH | 2M 2-8 °C | 2M 25 °C/ 60% RH |
| Assay Edaravone | 98.5 | 97.9 | 102.1 | 101.5 | 99.1 | 97 | 101.8 | 102.7 |
| pH | 4.52 | 4.03 | 4.23 | 4.16 | 5 | 4.17 | 4.45 | 4.40 |
| Oxidation Impurity | ND | 0.02 | 0.01 | 0.01 | ND | 0.02 | 0.01 | 0.01 |
| Trimer F Impurity | 0.07 | 0.11 | 0.04 | 0.05 | 0.06 | 0.17 | 0.04 | 0.05 |
| Dimer Impurity | ND | 0.01 | ND | ND | ND | ND | ND | ND |
| Single Max Unknown Impurity | 0.03 | 0.25 | 0.03 | 0.03 | 0.03 | 0.04 | 0.03 | 0.03 |
| Total Impurities | 0.13 | 0.83 | 0.12 | 0.22 | 0.14 | 0.42 | 0.14 | 0.23 |

The invention claimed is:

1. A stable pharmaceutical composition comprising:

(i) edaravone in an amount ranging from about 10 mg/mL to about 50 mg/mL;

(ii) at least one pharmaceutically acceptable solvent selected from the group consisting of water, alcohol, glycerin, propylene glycol, polyethylene glycol, and mixtures thereof; and (iii) a crystallization inhibitor selected from the group consisting of xanthan gum, xylitol, glycerin, hydroxypropyl methylcellulose, hydroxypropyl cellulose, hydroxyethyl cellulose, polyvinyl alcohol, polyvinylpyrrolidone, sorbitol, and mixtures thereof in an amount ranging from about 0.5% to about 50% by weight of the composition;

(iv) a preservative selected from the group consisting of benzoic acid and the sodium or potassium salts thereof, isopropanol, butyl alcohol, benzalkonium chloride, benzethonium chloride, benzyl alcohol, butylparaben, cetylpyridinium chloride, chlorobutanol, chlorocresol, cresol, dehydroacetic acid, ethylparaben, ethylparaben sodium, methylparaben, methylparaben sodium, phenol, phenylethyl alcohol, phenylethanol, phenylmercuric acetate, phenylmercuric nitrate, potassium benzoate, potassium sorbate, propylparaben, propylparaben sodium, butylparaben, sodium dehydroacetate, sodium propionate, sodium benzoate, sorbic acid, thimerosal, thymol, and combinations thereof;

(v) a sweetening agent selected from the group consisting of acesulfame, alitame, aspartame, cyclamate, saccharin, sucralose, acesulfame potassium or sodium cyclamate, sorbitol, xylitol, *magna* sweet 110, and combinations thereof;

(vi) a flavoring agent selected from the group consisting of natural flavors, artificial flavors, and combinations thereof;

(vii) a solubility enhancing agent selected from the group consisting of oils, surfactants, hydrophilic polymers, polyhydric alcohols, and mixtures thereof; and (viii) a stability enhancing agent selected from the group consisting of an amino acid; sodium chloride; sodium sulfate; ethylenediaminetetraacetic acid (EDTA), a metal ion; a natural or synthetic gum; a cellulosic derivative; a sugar; a sugar alcohol; a monosaccharide; a disaccharide; a polysaccharide; and combinations thereof; and wherein the pharmaceutical composition is a ready-to-use oral solution; and wherein edaravone is the only active pharmaceutical ingredient in the composition.

2. The pharmaceutical composition of claim 1, further comprising an antioxidant selected from the group comprising sodium bisulfite, l-cysteine hydrochloride, and mixtures thereof in an amount ranging from about 0.001% to about 10% by weight of the composition.

3. The pharmaceutical composition of claim 1, further comprising a buffering agent is selected from the group consisting of sodium dihydrogen phosphate monohydrate, disodium hydrogen phosphate anhydrous, citric acid, ascorbic acid, acetic acid, sodium acetate, adipic acid, benzoic acid, sodium benzoate, sodium citrate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium ascorbate anhydrous, sodium ascorbate monohydrate, sodium tartrate, and combinations thereof, in an amount ranging from about 0.001% to about 10% by weight of the composition.

4. The pharmaceutical composition of claim 1, wherein the pH ranges from about 2 to about 7.

5. The pharmaceutical composition of claim 1, wherein the preservative is present in an amount ranging from about 0.1% (w/w) to about 90% by weight of the composition, the sweetening agent is present in an amount ranging from about 0.001% to about 10% by weight of the composition, the flavoring agent is present in an amount ranging from about 0.001% to about 10% by weight of the composition, the solubility enhancing agent is present in an amount ranging from about 0.1% to about 90% by weight of the composition, and the stability enhancing agent is present in an amount ranging from about 0.001% to about 50% by weight of the composition.

6. The pharmaceutical composition of claim 1, wherein the composition is free of a preservative.

7. The pharmaceutical composition of claim 1, wherein the composition is stable at 2-8° C. for at least 6 months.

8. The pharmaceutical composition of claim 1, wherein the composition is stable at 25° C./60% RH for at least 3 months.

9. The pharmaceutical composition of claim 1, wherein the concentration of oxidation impurity is less than about 0.5% (w/w) as measured by HPLC, after being stored at 2-8° C. or at 25° C./60% RH for at least 6 months.

10. The pharmaceutical composition of claim 1, wherein the concentration of dimer impurity is less than about 0.5% (w/w) as measured by HPLC, after being stored at 2-8° C. or at 25° C./60% RH for at least 6 months.

11. The pharmaceutical composition of claim 1, wherein the concentration of trimer F impurity is less than about 0.5% (w/w) as measured by HPLC, after being stored at 2-8° C. or at 25° C./60% RH for at least 6 months.

12. The pharmaceutical composition of claim 1, wherein the concentration of edaravone is about 21 mg/mL.

13. The pharmaceutical composition of claim 1, wherein the concentration of edaravone is about 18 mg/mL.

14. The pharmaceutical composition of claim 1, wherein the solution is a ready-to-use solution.

15. The pharmaceutical composition of claim 1, wherein the quantity of water is up to about 50% (w/w) based on the total weight of the solution.

16. The pharmaceutical composition of claim 1, wherein the quantity of water is up to about 60% (w/w) based on the total weight of the solution.

17. The pharmaceutical composition of claim 1, wherein the quantity of water is up to about 70% (w/w) based on the total weight of the solution.

18. A stable pharmaceutical composition comprising:

(i) edaravone in an amount ranging from about 10 mg/mL to about 50 mg/mL;

(ii) at least one pharmaceutically acceptable solvent selected from the group consisting of water, alcohol, glycerin, propylene glycol, polyethylene glycol, and mixtures thereof;

(iii) crystallization inhibitor is present in an amount ranging from about 0.5% (w/w) to about 50% (w/w), (iv) preservative is present in an amount ranging from about 0.1% (w/w) to about 90% by weight of the composition, (v) sweetening agent is present in an amount ranging from about 0.001% to about 10% by weight of the composition, (vi) flavoring agent is present in an amount ranging from about 0.001% to about 10% by weight of the composition, (vii) solubility enhancing agent is present in an amount ranging from about 0.1% to about 90% by weight of the composition, and (viii) stability enhancing agent is present in an amount ranging from about 0.001% to about 50% by weight of the composition;

wherein the pharmaceutical composition is a ready-to-use oral solution;

wherein the composition is free of cyclodextrins; and wherein edaravone is the only active pharmaceutical ingredient in the composition.

* * * * *